United States Patent [19]

Kopp et al.

[11] 4,150,360
[45] Apr. 17, 1979

[54] METHOD AND APPARATUS FOR CLASSIFYING BIOLOGICAL CELLS

[75] Inventors: Richard E. Kopp, Smithtown; Joseph Lisa, Ronkonkoma; Jay Mendelsohn, Old Bethpage; Benjamin J. Pernick, Brooklyn; Harvey Stone, Flushing; Martin R. Wohlers, Cold Spring Harbor, all of N.Y.

[73] Assignee: Grumman Aerospace Corporation, Bethpage, N.Y.

[21] Appl. No.: 860,637

[22] Filed: Dec. 14, 1977

Related U.S. Application Data

[62] Division of Ser. No. 581,799, May 29, 1975, abandoned.

[51] Int. Cl.² ............................................. G06K 9/00
[52] U.S. Cl. .............................. 340/146.3 P; 250/550; 340/146.3 CA; 350/162 SF; 356/39; 356/71

[58] Field of Search .................. 350/162 SF; 356/71, 356/39; 250/550; 128/2 B, 2 G; 340/146.3 P; 364/726, 416

[56] References Cited

U.S. PATENT DOCUMENTS

| | | | |
|---|---|---|---|
| 3,563,634 | 2/1971 | Parks et al. | 350/162 SF |
| 3,689,772 | 9/1972 | George et al. | 350/162 SF |
| 3,873,970 | 3/1975 | McMahon et al. | 340/146.3 P |
| 3,947,123 | 3/1976 | Carlson et al. | 350/162 SF |

Primary Examiner—Leo H. Boudreau
Attorney, Agent, or Firm—Richard G. Geib; Mellor A. Gill

[57] ABSTRACT

A means of probing a biological cell sample with a optical source to determine the characteristics of the cell image by way of measuring parameters from its two dimensional Fourier transform. These techniques lead to a method of measuring discriminating parameters for cell classification.

11 Claims, 14 Drawing Figures

METHOD AND APPARATUS FOR CLASSIFYING BIOLOGICAL CELLS

This is a division of application Ser. No. 581,799 filed May 29, 1975, now abandoned.

FIELD OF THE INVENTION

This invention relates to an apparatus and a method for automatically detecting cell irregularities such as may be caused by cancer.

SUMMARY OF THE INVENTION

A widely used technique for reliably analyzing smears of body fluids is described in a publication entitled, Diagnosis of Uterine Cancer by the Vaginal Smear, by G. N. Papanicolaou and H. F. Trout, published by Commonwealth Fund, New York, 1943. In brief, Cancer cells which are exfoliated into body fluids are detectable upon microscopic analysis of stained smears of the body fluid by highly trained personnel. It has long been known as the Papanicolaou technique. Such technique involves highly trained personnel employed in a time consuming and tedious observation under microscope of a cell's:

(1) Nuclear Diameter,
(2) Cytoplasmic Diameter
(3) Nuclear Shape,
(4) Nuclear Chromatin,
(5) Cytoplasmic Stain Density,
(6) Nuclear Inhomogeneity,
(7) The relative parameters of the cell with respect to others and
(8) Cell Isolation.

The procedure employed was designed by a group of experts in the field of medicine.

As may be readily appreciated, the benefits of preventive medicine, especially in the case of cancer where early detection in many cases determines life or death, has led many to attempt to automate the cell classification process. One known prior art attempt is found in the U.S. Pat. No. 3,327,117 issued June 20, 1967 to a Louis A. Kamensky, which is directed to a means to sense the nucleus and cytoplasm changes that take place in a cancer cell from that of a normal cell by the use of an apparatus to probe the cell with an ultraviolet light energy of two wave lengths of a pre-determined order such that cell classification can be provided by electrical signals dependant upon the absorbtion profiles of both wave lengths by the cell under study.

Another prior art attempt of automating cell classification is shown by U.S. Pat. No. 3,497,690 issued Feb. 24, 1970 to Leon L. Wheeless Jr., et al. In this attempt the cells are stained by a Fluorochrome, rather than by the Papanicolaou technique, and subjected to an ultraviolet light source with subsequent measurement of the fluorescent response of the cell structure to provide its classification.

A principal object of this invention is to bring to the art of research in cytology and pathology the investigatorial attributes of Fourier transformation, i.e the use of the diffracted light from a cell image that may be collected optically in a single plane and electrically probed to obtain the spatial intensity in relation to its spectral frequency.

As will be readily appreciated by those skilled in the art of optics the illumination of an object by a light source will diffract the light into an optical pattern which has varying intensity at different points in the pattern. Such a diffraction pattern has no direct resemblence to the object, as an image, but is a collection of a series of overlapping diffraction patterns, each pattern due to individual features of the object. Such diffraction patterns are the result of the modification or diffraction of the light by the various points or details of the object or cell image.

While it is conceivable to utilize measuring apparatus to compute and indicate the spatial frequency of such deflected light it is considerably lens cumbersome to collect such diffraction pattern by a len or sensors and transform its various paths of light energy into a single plane. Such is the function of a Fourier transform apparatus in the art of optics.

This invention was conceived during an investigation that was studying coherent optical signal processing techniques for cytological investigations of, for example, exfoliated cells. These investigations focused directly on the primary morphological features of the cell.

The exfoliated cells are found in body fluids such as secretions from the female genital track, gastric fluid, sputum, or in various body cavities such as pleural fluid, peritioneal fluid, urine, cerebrospinal fluids, punctates expirmates or washings from epitheial surfaces, as were heretoforth collected from certain body sites for microscopic examination. In addition, spontaneously exfoliated cells can be supplemented by cells obtained directly from certain organs by the use of suitable instruments. Such cells maybe employed for detection and diagnosis of various pathological conditions.

Actually, as stated before, the invention is concerned with the problem of automating cytological evaluation by measuring heretofore subtle distinctions between test cell samples that fall within the capabilities of machine recognition.

More particularly, this invention relates to a process whereby cells, or high resolution cell images as by photographs or other means, are subjected to a coherent light source. The light is scattered, diffracted and/or refracted into a two dimensional Fourier spectrum of the cell or cell image. This will provide a variety of transform parameters functionally related to the cell diameter, nuclear diameter, nuclear density and other cell features, such as clumping of nuclear deoxyribonucleic acid (D.N.A.) that in combination greatly enhance the discriminatory capabilities of cell evaluation.

This invention, therefore, advances the prior art by the disclosure of a means to use the diffraction and refraction properties of coherent light for cytological screening and sample enrichment.

Another way of stating the object of this invention is to provide an apparatus and a process that will afford discrimination or classification of cytological samples by the computation and evaluation of various statistical discriminating functions that can be related to cell diameter, nuclear diameter, and nuclear density - all cytological discriminating parameters, as for example in tests for malignancy in exfoliated cervical cells as compared to normal cells, in cytopathology.

A still further object of this invention is to provide an apparatus and a process for the screening of cytological samples that will accommodate irregularities in cell shapes in studies of the cells.

Still another object of this invention is to provide apparatus and a process for screening of cytological samples whereby various statistical discrimination functions may be calculated, displayed and recorded.

The readers attention is directed to the article, "The Use of Coherent Optical Processing Techniques for Automatic Screening of Cervical Cytological Samples," by R. E. Kopp, et al. The Journal of Histochemistry and Cytochemistry, Volume 22, No. 7, 1974, pp 598–604 wherein a theory and some results of this invention has been set forth without discussion of the apparatus and processes to fulfill the above objects and others that will appear from the following drawings and detailed description of this invention.

DRAWING DESCRIPTION

With reference to the drawings accompanying this disclosure there is shown by:

FIG. 1, An isometric schematic illustration of a combination of apparatus that was used in carrying out the invention hereof;

FIG. 1A, An isometric illustration of a specific form of a combination of means that has used this invention showing the projection of a collimated light source to obtain a diffraction pattern for a cell to be classified by a radial scan.

FIG. 1B, An isometric illustration of an apparatus used in this invention in companion with the apparatus of FIG. 1A in an angular scan for measuring selective additional parameters to complete cell classification;

FIG. 2, A frontal view of a solid state electro-optical detector, as may be utilized in the apparatus and process of this invention, FIG. 2A, A frontal view of a fiber optic detector as may be utilized in the apparatus and process of this invention, FIG. 3, An isometric view of yet another form of a combination of apparatus, as may be created in a laboratory for carrying out the procedures of this invention;

FIG. 3A, A cross sectional view of an optical transducer used with the apparatus of FIG. 3;

FIG. 4, A schematic block illustration of the apparatus of this invention;

FIG. 5, A schematic block form of apparatus to provide computed indication of cell classification parameters;

FIGS. 6 and 7, Graphical illustrations of measured signature functions from the apparatus of FIG. 1A for three normal and three malignant cell structures measured by apparatus according to this invention;

FIGS. 8 and 9, Graphical illustrations of yet another measured signature function from the apparatus of FIG. 1B, for a normal and a malignant cell structure according to this invention; and FIG. 10, A graphical illustration of average measured parameters for two cell structures computed by apparatus according to this invention.

DETAILED DESCRIPTION

Figure 1:
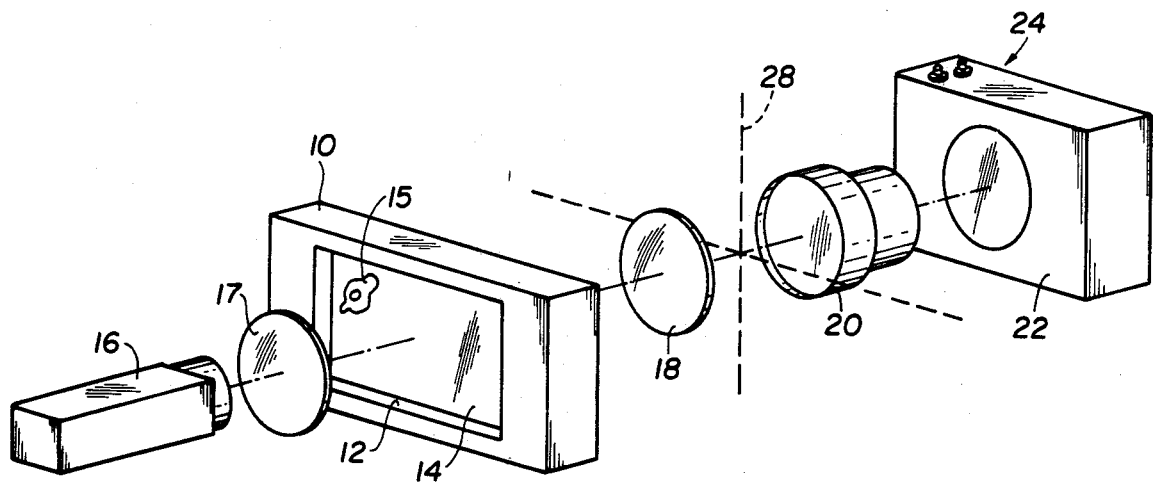

This invention is useful in the classification of cells, and it is particularly described with respect to the diagnosis of the cancer cells, whose various structure or morphological features, (sizes, ratio of nuclear diameter to cytoplasmic diameter, nuclear density, nuclear irregulatity) differ from that of a normal, non-cancerous, cell structure.

As will be readily appreciated in the performance of this invention, cell tissue smears are obtained and stained according to the Papanicolaou technique then fixed on a glass slide. Thereafter, and with particular reference to the embodiment illustrated in FIG. 1, a photograph is made of the cell structure, as by the use of a Nikon F camera body mounted onto a Nikon Su Ke microscope equipped with a trinocular head. It has been found that photographs bearing a desired contrast can be obtained by use of a 40X objective lens and 10X ocular employed with a $\frac{1}{2}$X relay leans to yield a 200X magnification at the film plane, and by the recording to the cell measured on K649F emulsion, 35 mm film. The high resolution capability, large contrast ratio, and large saturation density were found to be useful film characteristics for this purpose. The film records were then developed with D-19 developer for 10 minutes at 68 degrees Fehrenheit to achieve the large contract ratio desired.

The developed film was then mounted within a film transport 10 having an opening 12 for the exposure of the film 14 to a coherent beam from the laser 16 expanded to cover the film with a lens 17. The coherent light is scattered by the cell image forming a two dimensional angular Fourier Transform spectrum of the cell image 15. The angular spectrum is then projected by a lens 18 to a transform plane 28.

The Fourier transform or diffraction pattern from the lens 18 is then collected by a magnifying lens 20 and projected on a face of an optical detector 22 that is adapted to provide electrical signals for contacts 24 that will be indicative of various measured parameters of the diffraction pattern on the detector 22, as will be described hereinafter.

Figure 1A:
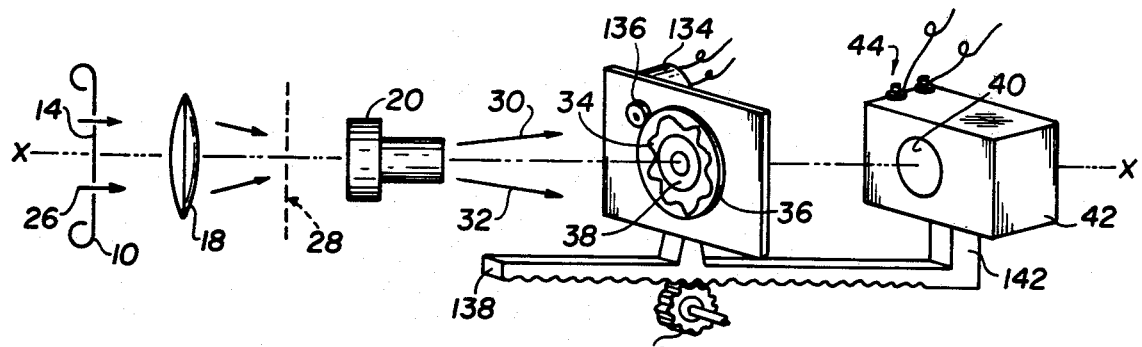
Figure 1B:
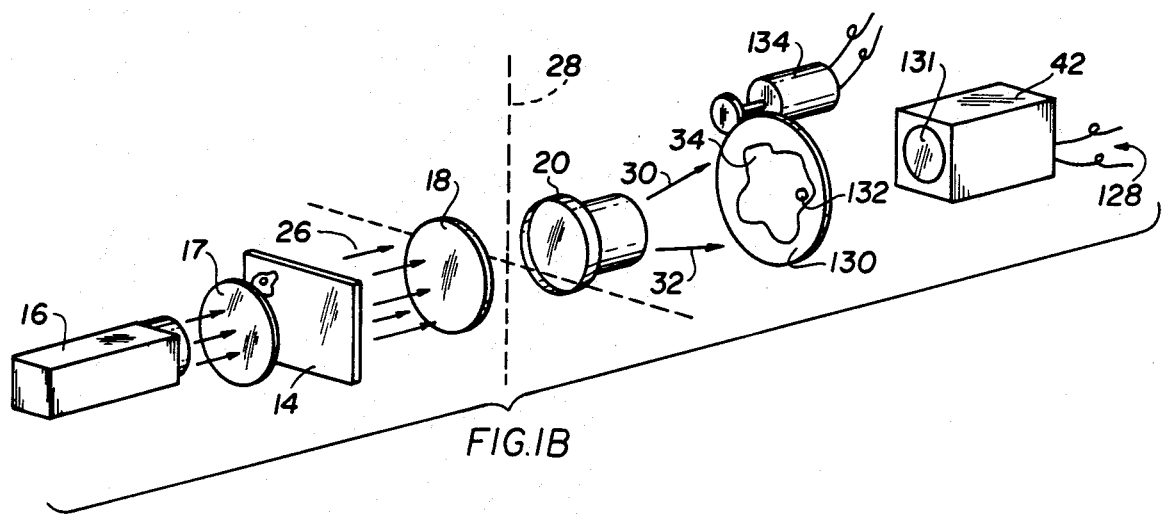

This is also shown with reference to FIGS. 1A and 1B which shows an alternative means of measuring various details of the diffraction pattern where the laser beam 26 generates the Fourier transform to a diffraction plane 28 that is expanded by the microscope 20, as shown by the energy lines 30 and 32 to project a diffraction pattern 34 on a mask 36. The mask 36 and photomultiplier 42 has been substituted in this embodiment for the optical detector 22 of FIG. 1. As seen, mask 36 has an aperture 38 that permits the passage of light energy of a portion of the diffraction pattern to the sensor lens opening 40 of a photomultiplier 42, as will be readily familiar to those skilled in the art of devices of measuring light intensity. The photomultiplier 42 is provided with electrical terminals 44 that are the equivalent of terminal 24 for the feeding of the electrical signals generated thereby, whose amplitude is a function of the intensity of the light energy transmitted by the mask.

Another means of measuring other specific features of the diffraction pattern is shown in FIG. 1B. Angular scans of the light intensity in the diffraction plane we taken using a rotating mask 130 containing a small hole 132 located at a radial distance from the center of the diffraction plane. The mask was rotated mechanically by drive 136 of motor 134 through 360° and the light energy passing through the small hole was collected by a means 131 such as a collector lens and photomultiplier.

Figure 2:
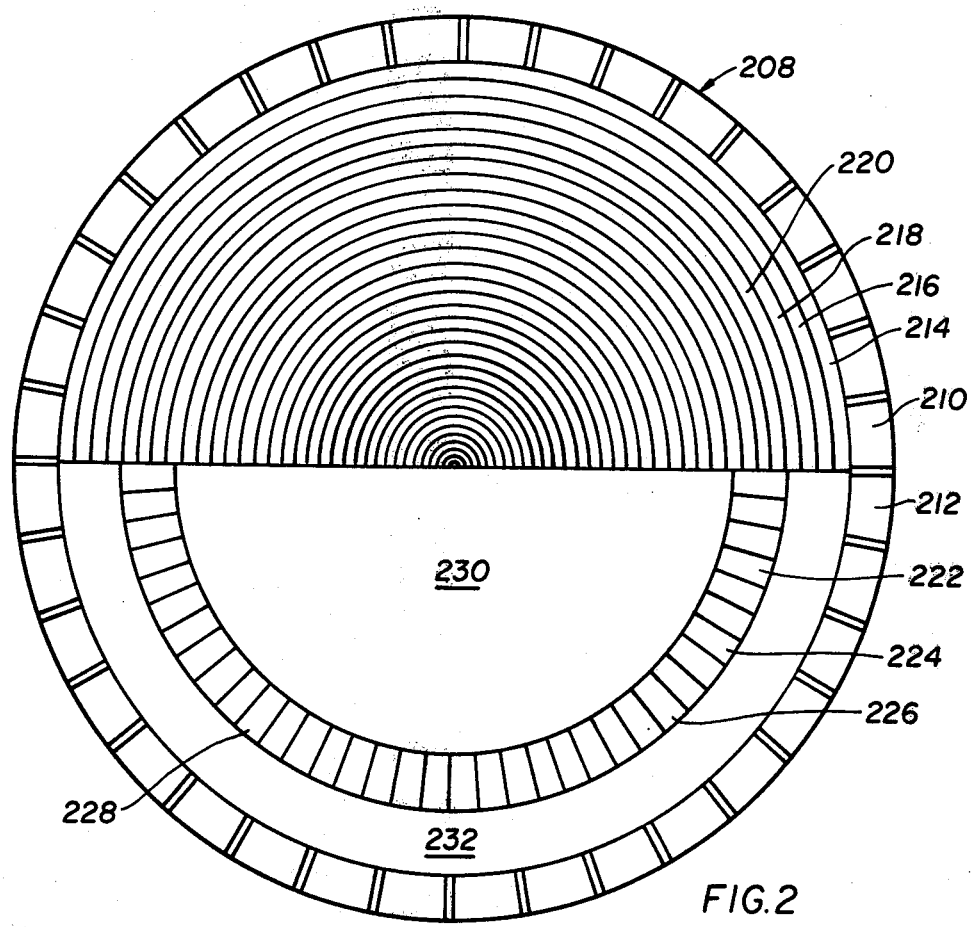

One may also combine the feature measuring capability of the two mechanically activated systems shown in FIGS. 1A and 1B, by a single solid state electro-optical detector as shown in FIG. 2.

Specifically, there is shown in FIG. 2 a solid-state detector having an annular plate 208 comprising a plurality of semiconductor fabricated areas layed out in geometric patterns. More particularly, the plate face is divided into two semi-circular halves 210 and 212. There is fabricated by the use of the well known semiconductor technology a plurality of individual rings, rings 214, 216, 218 and 220 being specifically called out by way of example, in the upper half 210. On the face of the lower half 212 there is similarly provided a plurality of partial wedge shaped active areas, wedges 222, 224, 226 and 228 being called out by way of example leaving non-active surfaces 230 and 232 in the lower semi-circular half 212. Conductors (not shown) lead from each of the rings 214 etc. and wedges 222, etc. so as to provide for the conducting of an electrical signal in accordance with the light energy on these rings or wedges, as will also be readily familiar to those skilled in the art of light sensitive semi-conductor technology. The detector shown is an improvement upon the type as disclosed by U.S. Pat. No. 3,689,772. The improvement being the elimination of unwanted confusion which would be caused by large area wedges.

It has been found that by this design of the detector 22 it is possible to automate the process of cell classification to a greater degree than is possible by the use of the processes involved with apparatus of FIGS. 1A and 1B. This results from the fact that the rings 214, etc. being each able to provide an electrical signal indicative of the total energy about the individual ring will provide a radial scan similar to that permitted by the mask 36; and the limited areas of the angular position of the partial wedges 222, etc. will provide an electrical signal indicative of an angular scan of any light intensity similar to that which will be provided by the use of the mask 130.

Figure 2A:
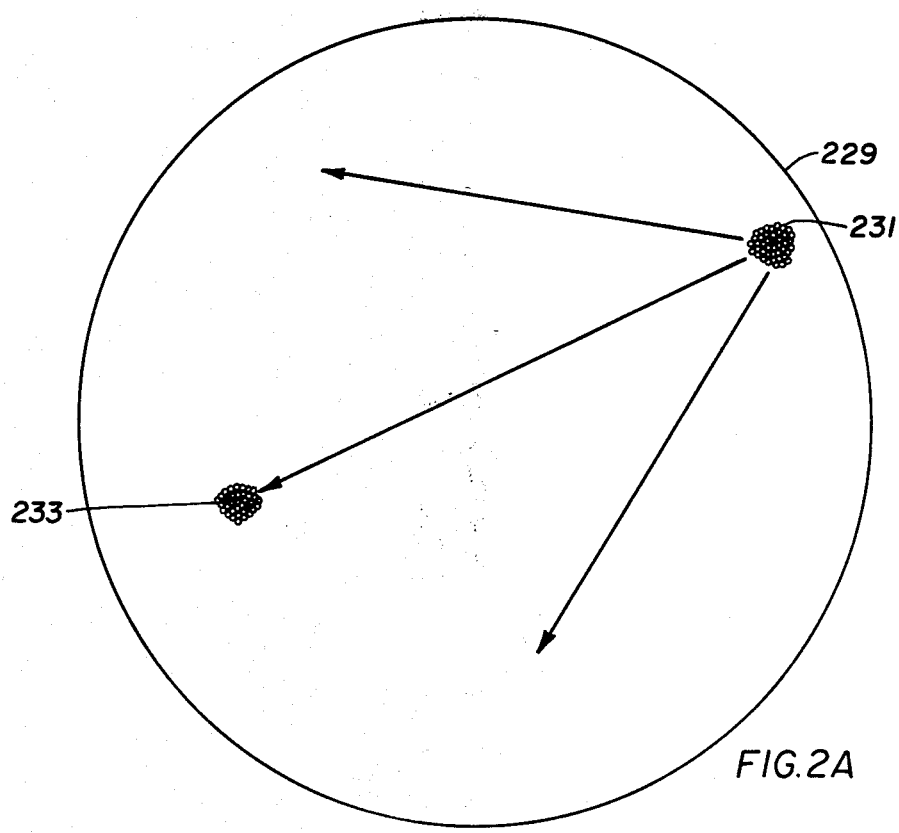

A fiber-optic detector may also be used in place of a photomultiplier or a solid-state detector. Such a fiber-optic detector is shown by FIG. 2A to comprise a disc 229 mounting of bundles of individual light conducting fibers 231, 233, etc. Each bundle of fibers, as will be readily understood to those skilled in the art, will be connected with individual photo sensitive means such as phototransistors (not shown) to furnish individual electrical signals to a computer or similar measuring means, to indicate in the same fashion as the other detector means the light energy within the Fourier Transform pattern. Such a bundle of optical fibers can be connected in the measuring circuit in almost any desired way to provide analysis of all or any part of the pattern by rendering all or some bundles effective in providing electrical analysis signals.

Figure 3:
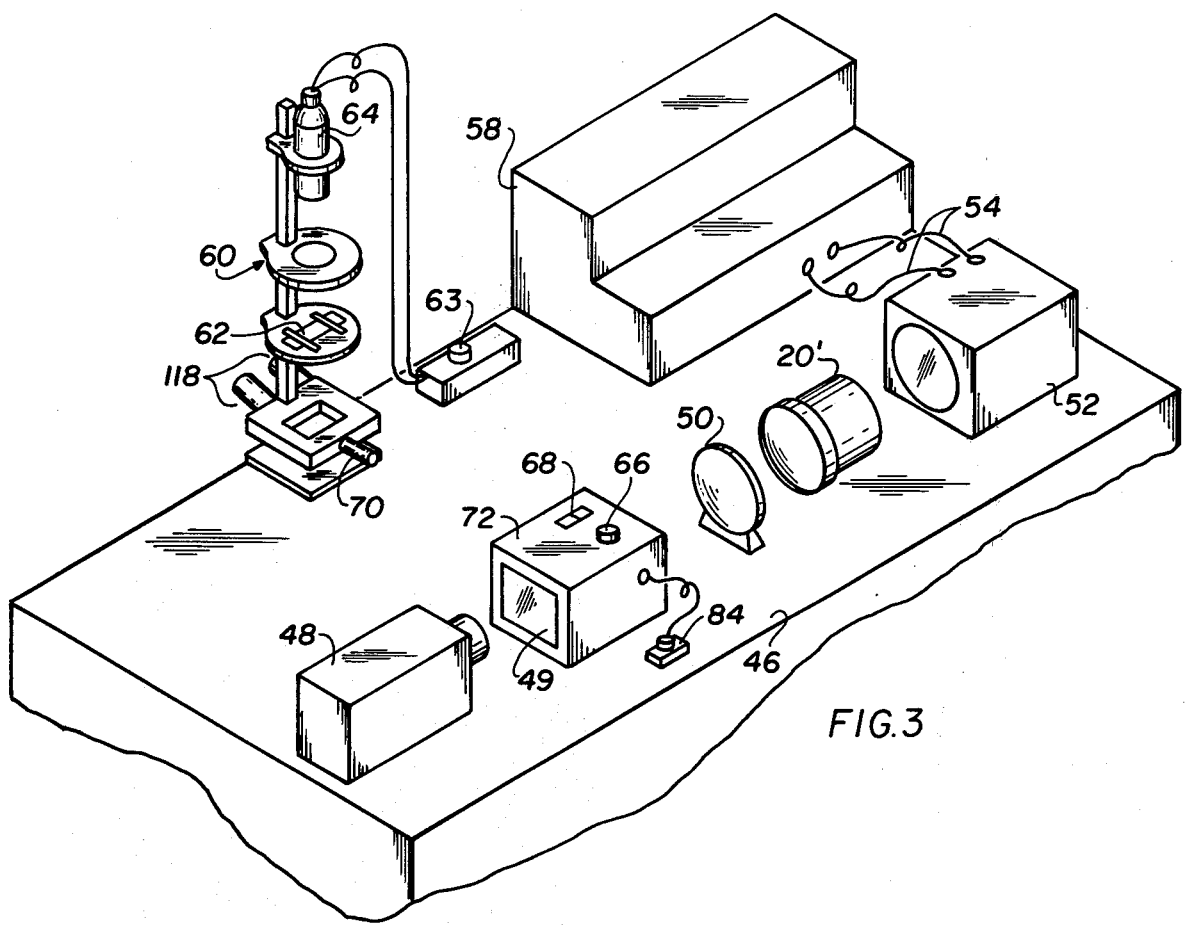
Figure 3A:
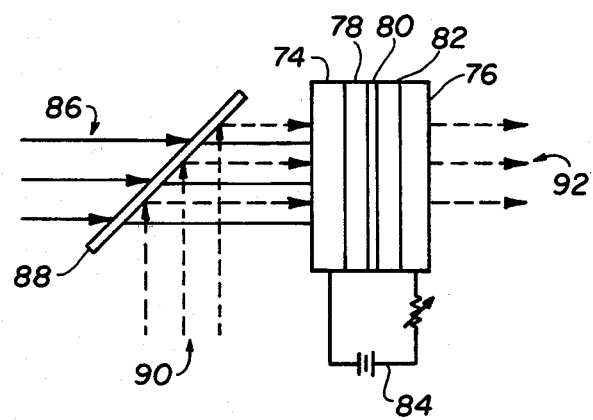

With reference now to FIGS. 2 and 3A there is shown a still further form of apparatus that embodies the principles of this invention. More particularly, there is shown a stable platform 46 on which is mounted a laser 48, an expanding lens 49, a Fourier transform lens 50 and a solid-state electro-optical detector within a housing 52 that is connected by leads 54 to a minicomputer 58 for taking the measurements of the detector 52 and providing a computed indication thereof. In this embodiment a projection microscope 60 is utilized to view the cell tissues prepared, as aforesaid, and placed on the microscope stage by the glass slide 62. As schematically shown, the projection microscope 60 has a means 64 to focus light, such as a variable intensity projection bulb, upon the glass slide 62 in accordance with a variable control 63, whereby a projection, as by a lens 70, of the cell image may be delivered to a optical transducer means within a housing 72. At the same time an operator can also view the glass slide material by means of eyepiece lenses 118. The contrast of the image on the transducer may be varied by variable resistance control 66 as shown by indicator 68. The optical transducer is more particularly described with reference to FIG. 3A to consist of a sandwich between conductive coated glass flims 74 and 76 of a photoconductive layers 78 and 82 surrounding a layer 80 of electrically activated material with variable optical transmission properties. A power source 84, illustrated as a battery in FIG. 3A and provided by means of an electrical outlet in FIG. 3 is connected by appropriate conductors to the transducer shown, as will be readily appreciated by those skilled in the art. A more particular description of a typical transducer such as may be required herein is shown by U.S. Pat. No. 3,732,429 issued May 8, 1973. In brief a photoconductive cadmium sulfide layer 78 functions to convert the incoherent light image 90 passing through a beam splitter 88 also projecting the coherent light energy 86 of the laser beam 48 (see FIG. 3) projected on the conductive coated glass film 74 into a flow of current through a liquid crystal layer 80. The liquid crystal 80 then responds to the current flow by changing its optical transmission; in particular, it becomes translucent such that the image in the liquid crystal layer is impressed onto the laser beam 86 after the beam passes through the device to provide an output beam 92 projecting a coherent image of the cell on slide 62 through the Fourier transform lens 50. Therefore, one may view the transducer as an instantaneously developed film transparency in that the projection therefrom is the same as if one exposed a piece of film to an incoherent light image, placed the developed film transparency in a path of a laser beam, and observed the outcoming laser beam diffraction pattern, as by the apparatus illustrated in FIGS. 1 and 1A. Furthermore, the image transparency (density & contrast) may be varied by adjusting the exciting voltage applied to it as by control 66.

Figure 4:
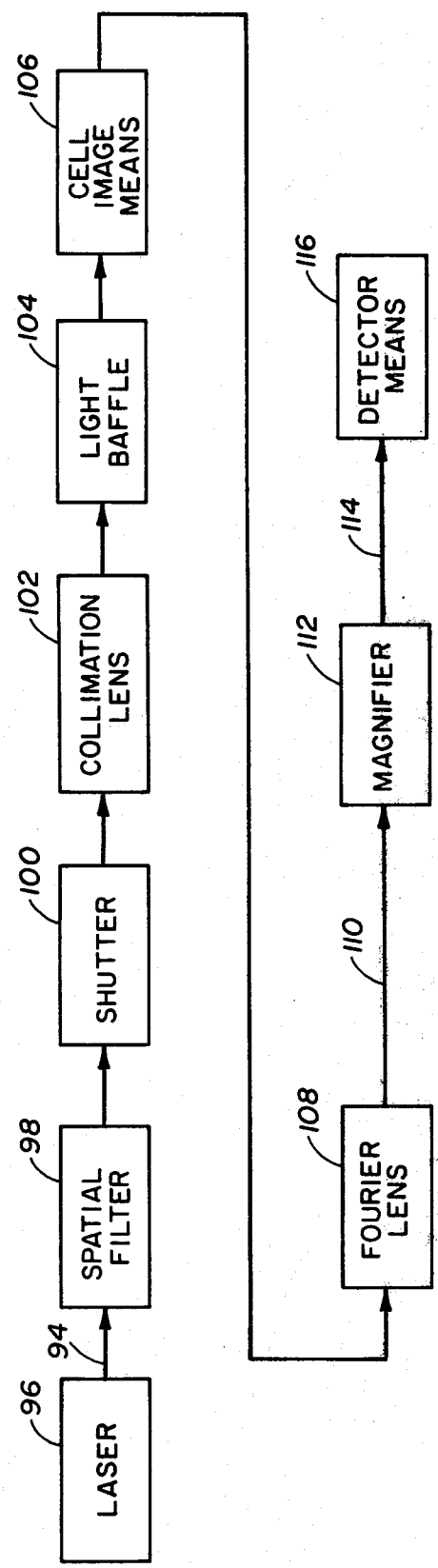

A schematic illustration of the general means for generating and then measuring cell diffraction patterns is shown in FIG. 4 and includes the various previously described system. The laser beam 94 from a laser 96, such as a Spectra Physics model 124A, is expanded with a lens and a pinhole combination such as a 4.5 mm lends and 6.8 micron pinhole in a spatial filter 98, such as a Spectra Physics model 330. A mechanical shutter 100 is employed between the filter 98 and a collimation lens 102, such as a Tropel f-4, 200 mm lens, for exposure control. After collimation, the center portion of the expanded beem is transmitted through a rectangular aperture (typically 25/32 in. × ½ in.) formed by a light baffle 104, such as a Conductron four-way adjustable aperture model, to a film holder or optical transducer 106. If a film holder is used, it has been found that an individual frame of a 35 mm cell image film strip can be held by clamping it between two optical flats, wetted with a refractive index matching liquid. Thereafter, the light diffracted by the cell image is collected with a transform lens 108 to provide a transform pattern 110. However, as the transform in the back focal plane of lens 108 may be too small for covenient observation, a short focal length magnifier 112 is used to enlarge the diffraction pattern image. In one embodiment of the optical system the magnification factor used thus far was about 40X, and the equivalent spatial frequency scale in the cell image plane was about 1000 cycles/mm per cm. The magnified diffraction pattern 114 (34 in FIG. 1A) is then projected upon appropriate detector system 116 as described above.

With the aforedescribed measuring equipment there is permitted the recording of signals from radial and angular information of the Fourier transform spectrum upon a magnetic tape for data storage and handling.

Figure 5:
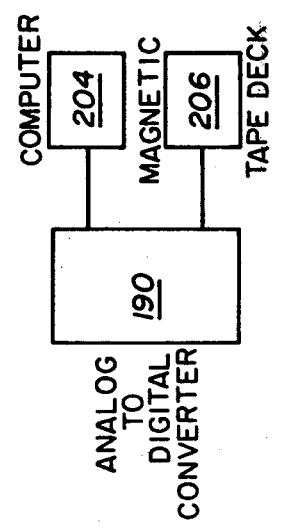

Reference should now be made to FIG. 5 showing that subsequent to the recording on the magnetic tape such tapes may be digitized by an instrument 190.

Final processing of the raw, digitized data is achievable by a computer 204 and at the same time provided to a magnetic tape machine 206 to permit retention of the digitized data for subsequent checking of the computation, if necessary.

As will appear hereinafter, the aforesaid apparatus will permit the generation of the graphical illustrations of FIGS. 6 through 10 from measured data for the comparison of a normal cell with a malignant cell. At the same time the apparatus provides signals that may be utilized in a statistical analysis that will utilize the fundamentals of various statistical decision procedures such as the Baysian decision process in pattern classification.

Now in particular regard to the process that is only permitted by the aforedescribed apparatus in the classification of cell tissue, and more particularly exfoliated samples such as are presently subjected to microscopic examination in the screening of cervical cell samples for determination of cancer, the normal process hereof involves first the step of the optical generation of a two dimensional Fourier transform. This involves the use of the cell image 15 (see FIG. 1) to spatially modulate the collimated laser beam thereby causing a diffraction of coherent light which is then collected by a Fourier transform lens located one focal length behind the image plane.

At a distance of one focal length behind the lens, the transverse spatial distribution of optical energy is functionally related to the modulated light immediately behind the film. This relationship is the two-dimensional Fourier transform given by:

$$F(w_x, w_y) = \int \int f(x_o, y_o) e^{-j(w_x x_o + w_y y_o)} dx_o dy_o \quad (1)$$

where transform size scaling is determined by the wavelength ($\lambda$) of the coherent light and the focal length (f) of the lens:

$$w_x = 2\pi x_f / \lambda f, \quad w_y = 2\pi y_f / \lambda f \quad (2)$$

where F is the Fourier transform of the cell image f, and the variables $x_f$ and $y_f$ are the cartesian coordinates in the transform plane.

There are several properties of the Fourier transform relationship which prompt the use of this approach as a screening device. The distribution, $F(w_x, w_y)$, is centered on the optical axis of the lens, with 180° symmetry in the transform plane, and its amplitude is independent of the location of the cell image on the film. This circumvents the problem of search for a particular image or feature of the image within the field of view of an instrument. Similar sized features in the cell contribute energy over the same region of the spectrum with small sensitivity to their precise shape and independent of their location within the image. Although it is not readily apparent from Eq. (1), there is an inverse relationship between the size of the image and the region of the Fourier spectrum containing the energy diffracted by the image—that is, small objects have large spectra and large objects have small spectra. These properties are attractive from an instrumentation point of view when considering a screening device. It is again worth mentioning that the relationship given in Eq. (1) is not highly sensitive to cell image motion along the optical axis, as in the case in scanning systems which require elaborate automatic focusing systems.

A more complete discussion and analysis of the optical generation of two dimensional Fourier transform can be found by reference to the books INTRODUCTION TO FOURIER OBJECTS by J. W. Goodman, McGraw Hill, N.Y. 1968, pp. 77–83 and AN INTRODUCTION TO COHERENT OPTICS AND HOLOGRAPHY by G. W. Stroke, Academic Press, N.Y. 1966, pp. 70–96.

The Fourier transform pattern of all the cells classified to date were subsequently analyzed quantitatively by measuring both the average radial distribution of light energy in the transform and also the angular variation at selected radial positions in the transform plane. The average radial energy distribution was measured using the apparatus shown schematically in FIGS. 1A and 1B. A spectrum sampling mask was made consisting of an open annulas 38 of radius $r_o$ and width $\Delta r$. This mask was located after the Fourier transform lens 18 and in front of a photomultiplier tube 42 which measured the integrated light intensity within the annulus. The mask and photomultiplier were then moved in unison along the optical axis of the transform lens, i.e., along the x-axis in FIG. 1A, and the outputs recorded as a function of x. As the origin of the x-axis is located at the point where the rays of light constituting the transform have an apparent focus, the spreading bundle of these rays has a distribution of intensity along any plane (defined by $x-x_o$) that is given approximately as $$I(r,\theta)|_{x=x_o} = \frac{\left|F\left(\frac{ar}{x_o}, \theta\right)\right|^2}{x_o^2 + r^2} \quad (3)$$

where $F(\rho, \theta)$ is the Fourier transform expressed in polar coordinates $\rho, \theta$ and $\rho^2 = w_y^2 + w_y^2$; r the radial position in the spreading bundle of rays; and the factor $ar/x_o$ contains the scale factor "a" of the optical system indicating the linear dilation of the beam, and the factor $1/x_o^2 r^2$ acconds for the usual squarelaw fall-off of the light intensity. The output of the photomultiplier $M_{out}$ is proportional to the integrated light coming through the annulus in the mask when it is located at an artitrary position, or explicitly:

$$M_{out}(x) = \int_0^{2\pi} \int_{r_o}^{r_o + \Delta r} \left|F\left(\frac{ar}{x}, \theta\right)\right|^2 r\, dr\, d\theta \quad (4)$$

It may be necessary to have webs to support the annulus in the mask. The webs will block some of the light. (However, the webs are useful in obscuring light in the diffraction pattern due to the rectangular aperture geometry).

To gain some insight into the nature of this measurement we will assume that the annulus width $\Delta r$ is sufficiently small so that:

$$M_{out}(x) = \frac{r_o \Delta r}{x^2 + r_o^2} \int_0^{2\pi} \left|F\left(\frac{ar_o}{x}, \theta\right)\right|^2 d\theta \quad (5)$$

$$\approx \frac{2\pi r_o \Delta r}{x^2 + r_o^2} \left|F\left(\frac{ar_o}{x}, \theta\right)\right|^2_{avg}$$

where the average pertains to the average taken over the angular variations. If $r_o$ and $\Delta r$ are fixed and x is varied we may sample the average $|F|^2$ at different values of radial spatial frequency, $\rho$. Thus assuming that the optical scale factor "a" is selected so that:

$$ar_o/x = \rho \tag{6}$$

we find that:

$$M_{out}(x) = \frac{2\pi \Delta r/r_o}{a^2 + \rho^2} \rho^2 |F(\rho,\theta)|^2_{avg} \tag{7}$$

Finally, with a spatial frequency satisfying a we have:

$$M_{out}(x) = \frac{2\pi \Delta r}{a^2 r_o} \rho^2 F^2_{avg} \sim \rho^2 |F|^2_{avg} \tag{8}$$

or an output that a proportional to $\rho^2$ times the intensity squared of the transform.

Different masks were constructed having $\Delta r/r_o$ ratios of 0.25 and 0.1 and were used to measure $\rho^2|F|_{avg}^2$ over two spatial frequency ranges: 10 to 100 cycles/mm; and 100 to 1000 cycles/mm, respectively referred back to the microscope slide. The data was reduced further and normalized by dividing each output by the total light energy E in the Spectrum to complete the step of conducting a radial scan of the diffraction pattern. In such scan runs data from one of the masks produced the curves of FIGS. 6 and 7. These curves are measures of the average radial distribution of normalized energy in the transforms and one may regard them as measures of $\rho^2|F|_{avg}^2$, bearing in mind the above, particularly the fact that the width of the annulus is not arbitrarily small but in fact $\Delta r/r_o \approx 0.25$ or 0.1 with the greatest error appearing in the low frequencies. Such curves may be regarded as a signature functions for the particular cell.

In addition to the annulus data, angular scans of the light intensity in the Fourier transform were made with a mask containing a small hole 132 located at a radial distance from the center of the transform. Actually this step includes placing the hole at four different radial distances corresponding to spatial frequencies of 430, 485, 565 and 630 cycles/mm. The hole diameter corresponds to 65 cycles per millimeter. The mask was rotated through 360°, measuring the optical energy passing through the small hole as a function of the angular position in the Fourier transform. This was done for each of the four radial distances mentioned. The curves of the angular variations are also shown for the cells by FIGS. 8 and 9 and may be regarded as another signature function for the cell. The ordinate in each case is in arbitrary relative scale, nevertheless the results can be compared from curve to curve since the maximum value on each scale is related to the others in the set.

Figure 6:
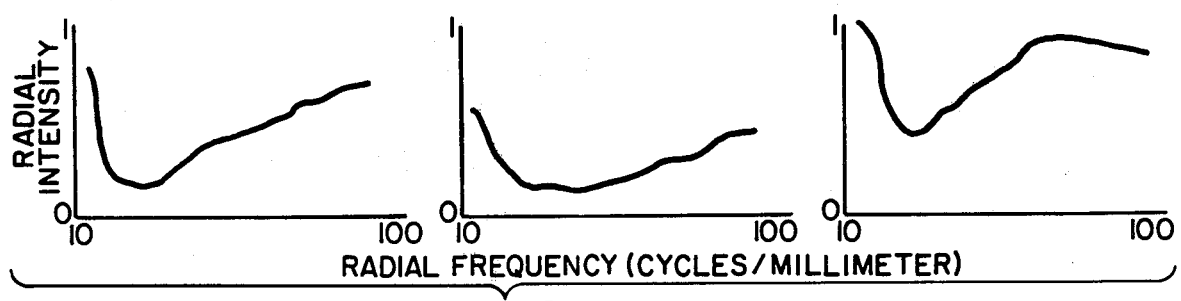
Figure 7:
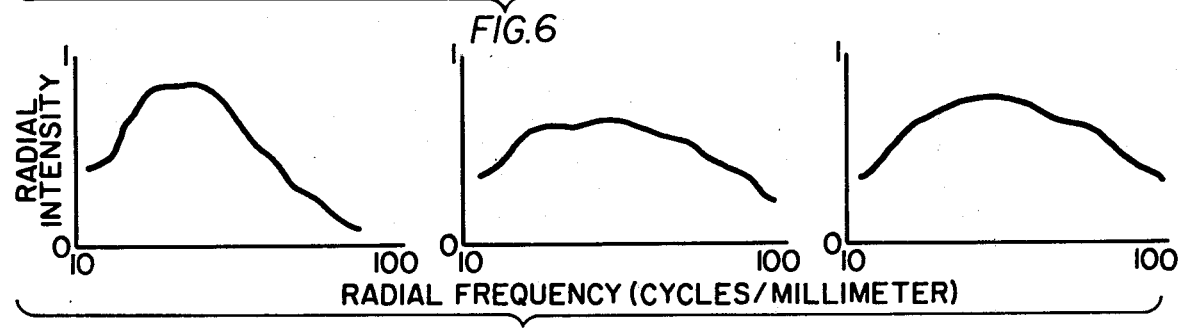

It should be noted that the curves of FIG. 6 are the result of the use of the apparatus of this invention in screening normal cell tissue; whereas the curves of FIG. 7 are a similar result in the screening of malignant cell tissue. The concave shape of the curves of FIG. 6 for the normal cells is readily contrasted with the convex shape of the curve for the malignant cells, whereby providing a means to distinguish normal and malignant cells by the slope of their radial distribution curve in a low frequency region, such as 10 cycles/mm, with normal cells having smaller slopes than the malignant cells.

Figure 8:
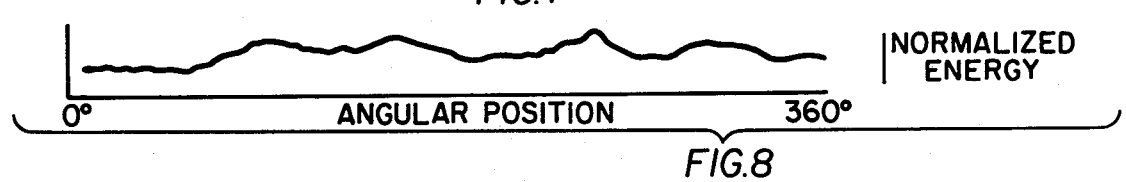
Figure 9:
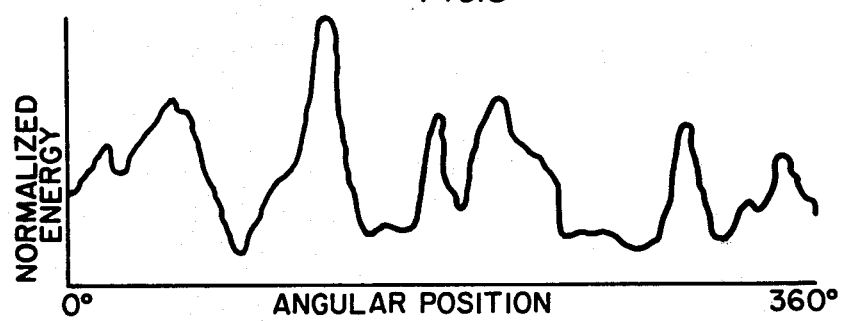
Figure 10:
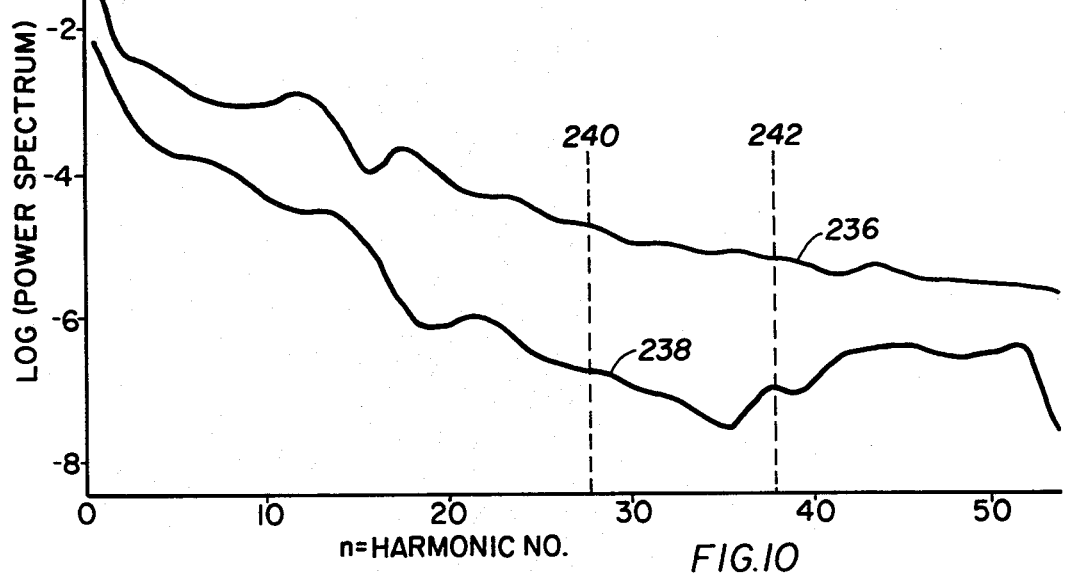

With more particular regard to FIGS. 8 and 9, angular scans of malignant cells (shown by FIG. 9) tend to have larger variations than the scans for the normal cell as shown by FIG. 8. This was investigated further by means of a power spectral analysis of the angular scan curves. With reference to FIG. 10 there is shown the average power spectrum for a group of malignant cells (trace 236) and a group of normal cells (trace 238). It should be noted from FIG. 10 that there is a range illustrated between the dotted lines 240 and 242 where one can find a wide separation of the average power spectrum density for malignant and normal cells within which machine measureable features would be less subject to classification errors than in other areas of the average power spectrum density for these cells.

Data collected from a group of cells was examined extensively and various parameters were abstracted from this data to be used for discriminating cell features. These parameters or features included the total light energy in the transform of the cell, the slope of $\rho^2 F^2_{avg}$ (the slope of the product of the square of the radial frequency times the average radial distribution of light energy in the transform), the variance of $\rho^2 F^2_{avg}$ over a range of valves of $\rho$, the variance of $|F|^2$ over angular coordinates, and the total energy in a portion of the power spectrum of the angular variation of $|F|^2$, etc. To be explicit, some of the parameters are given by the expressions:

1. Total energy:

$$E = \int_0^\pi d\theta \int_0^\infty \rho |F(\rho,\theta)|^2 d\rho \tag{9}$$

where ($\rho$ represents the radial spatial frequency coordinate, $\theta$ the angle, and $F(\rho,\theta)$ the Fourier transform distribution in polar coordinates):

2. Slope of $\rho^2 F^2_{avg}$ in the range a thru d (cycles/mm) normalized to total energy:

$$S = \frac{\left[ \int_0^\pi d\theta \int_a^b \rho^2 |F(\rho,\theta)|^2 d\rho \right] - \left[ \int_0^\pi d\theta \int_c^d \rho^2 |F(\rho,\theta)|^2 d\rho \right]}{E} \tag{10}$$

where a, b, c and d are specific radial positions of the selected range of radial spatial frequency, such as 10, 20, 30 and 40 cycles/mm.

3. Variance of $\rho^2|F|^2_{avg}$ in a second range e to f cycle/mm normalized to total energy:

$$V = \underset{\rho = e \text{ to } f}{avg} \left\{ \left[ \rho^2 \int_0^\pi \frac{|F(\rho,\theta)|^2 d\theta}{E} \right]^2 \right\} - \left\{ \underset{e \text{ to } f}{avg} \left[ \rho^2 \int_0^\pi \frac{|F(\rho,\theta)|^2 d\theta}{E} \right] \right\}^2 \tag{11}$$

where e to f is the specific radial position of the beginning and end of the second range selected such as 10 to 100 cycles/mm.

4. Variance of angular distribution of intensity in range g to h cycles/mm.

$$\text{Angular } V = \text{avg}_{\theta = 0 - \pi}\left\{\left[\int_g^h \rho|F(\rho,\theta)|^2 d\rho\right]^2\right\} - \qquad (12)$$

$$\left\{\text{avg}\left[\int_g^h \rho|F(\rho,\theta)|^2 d\rho\right]\right\}^2$$

where g to h is the specific radial position of the beginning and end of the third range selected such as 500 to 600 cycles/mm.

5. Total energy in a portion of the power spectrum of the angular distribution of intensity in the range from g to h cycles/mm:

$$\text{Angular } E = \sum_{n=i}^{m} a_n^2 \qquad (13)$$

where i to m are adjustable portions of the power spectrum such as over the 12$^{th}$ to 19$^{th}$ harmonic.

$$a_n = \frac{1}{2\pi}\int_0^{2\pi}\left(\int_g^h \rho|F(\rho,\theta)|^2 d\rho\right)e^{-jn\theta}d\theta$$

In the case where the solid state detector of FIG. 2 was employed to measure the features, we must approximate the various parameters defined above using the sampled ring and wedge outputs from the detector. Thus the ring outputs of the detector are:

$$V_r(I) = \int_0^\pi d\theta \int_{\rho_1(I)}^{\rho_2(I)} \rho|F(\rho,\theta)|^2 d\rho, \ I = 1, ..., 32 \qquad (14)$$

Where $\rho_1(I)$ and $\rho_2(I)$ are the inner and outer radii of the I$^{th}$ ring, and the wedge outputs are:

$$V_w(I) = \int_{\theta_1(I)}^{\theta_2(I)} d\theta \int_{500}^{600} \rho|F(\rho,\theta)|^2 d\rho, \ I = 1, ..., 32 \qquad (15)$$

where $\theta_1(I)$ and $\theta_2(I)$ are the angular coordinates of the sector forming the wedge and 600 and 500 are two frequency ranges. The fact that the Fourier plane detector presently in use provided a "sampled output" of the transform of the cell images required a variety of approximations to be made to obtain approximate values for the five desired features. For example, to approximate the desired integrals of $\rho^2|F|^2$ used in the calculations of slope, we approximated:

$$\int_0^\pi d\theta \int_{30}^{40} \rho^2|F(\rho,\theta)|^2 d\rho \approx \frac{\rho_2(6) + \rho_1(6)}{2}V_r(6) + \qquad (16)$$

$$\frac{\rho_2(5) + \rho_1(5)}{2}V_r(5)$$

where for the particular detector in question ring's 5 & 6 spanned the range of $\rho$ from 30 to 40 cycles/mm which implies that the approximation:

$$\int_{\rho_1}^{\rho_2} \rho^2|F|^2 d\rho \approx \frac{\rho_2 + \rho_1}{2}\int_{\rho_1}^{\rho_2}\rho|F|^2 d\rho \qquad (17)$$

was used. Similarly in the variance of $\rho^2|F|^2$, we used the approximation $$\rho^2|F(\rho,\theta)|^2 \approx \frac{\left(\frac{\rho_2(I) + \rho_1(I)}{2}\right)}{\rho_2(I) - \rho_1(I)}\int_{\rho_1(I)}^{\rho_2(I)}\rho|F|^2 d\rho \qquad (18)$$

which assumed $$\int_{\rho_1}^{\rho_2} \rho|F|^2 d\rho \approx (\rho_2 - \rho_1)\rho_{avg}|F|^2_{avg} \qquad (19)$$

In a similar way we used $$\int_{g=500}^{h=600}\rho|F(\rho,\theta)|^2 d\rho \sim \left[\int_{g=500}^{h=600}\rho|F(\rho,\theta)|^2 d\rho\right]\Delta\theta \qquad (20)$$

to define the angular distribution of intensity to be used in obtaining the last two features. Finally, in lieu of measuring the total energy in the specified portion of the spectrum of the angular data by computing the Fourier coefficients, $a_n$, a digital filtering technique was employed. Specifically, a digital filter operation was formed that used a four-pole Butterworth approximation to a band-pass filter with pass band from the 12$^{th}$ through 19$^{th}$ harmonic. The angular distribution or wedge data was then filtered, and the variance of the filtered signal was obtained. (The variance was used rather than the total energy of the signal to improve the approximation—with an ideal band-pass filter, the output should have zero mean.)

Then, as will be obvious to those skilled in the art, the following six features were computed from the detector output where five features are approximations to the basic five features identified previously, and a sixth (the third listed below) was an attempt to use a simplified version of the variance of the radial information: (the expressions used applied to a specific solid state detector manufactured by Recognition System Incorporated which had 32 rings and 32 wedges. Moreover a mask as shown in FIG. 2 was placed over the detector so that only the portion of light in the range of 500–600 cycles/mm fell on the 32 wedges).

1. Total energy:

$$E1 = \sum_{n=1}^{32} V_r(I) \qquad (21)$$

2. Slope of $\rho^2|F|^2$ in the range 10–40 cycles/mm normalized to total energy:

$$S1 = \left[\frac{\rho_2(6) + \rho_1(6)}{2}V_r(6) + \frac{\rho_2(5) + \rho_1(5)}{2}V_r(5)\right]/E1 \qquad (22)$$

$$- \left[\frac{\rho_2(3) + \rho_1(3)}{2}V_r(3) + \frac{\rho_2(2) + \rho_1(2)}{2}V_r(2)\right]/E1$$

3. Variance of radial intensity from 10–100 cycles/mm normalized to total energy:

$$V1 = \frac{\sum\limits_{I=1}^{13}\left[V_r(I) - \frac{\sum\limits_{I=1}^{13} V_r(I)}{13}\right]^2}{13(E1)^2} \quad (23)$$

4. Variance of $\rho^2|F|^2$ in the range 10–100 cycle/mm normalized to total energy:

$$V2 = \frac{\sum\limits_{I=1}^{13}\left[\frac{\left(\frac{\rho_2(I)+\rho_1(I)}{2}\right)}{\rho_2(I)-\rho_1(I)}V_r(I) - \sum\limits_{I=1}^{13}\frac{\left(\frac{\rho_2(I)+\rho_1(I)}{2}\right)}{\frac{\rho_2(I)-\rho_1(I)}{13}}V_r(I)\right]^2}{13(E1)^2} \quad (24)$$

5. Variance of angular distribution of intensity in the range 500–600 cycles/mm:

$$V3 = \frac{\sum\limits_{I=1}^{32}\left[V_w(I) - \frac{\sum\limits_{I=1}^{32} V_w(I)}{32}\right]^2}{32} \quad (25)$$

6. Total energy in a portion of the spectrum of the angular distribution of intensity in the range from 500–600 cycles/mm:

$$V4 = \frac{\sum\limits_{I=1}^{32}\left[Z(I) - \frac{\sum\limits_{I=1}^{32} Z(I)}{32}\right]^2}{32} \quad (26)$$

where $$Z(I) = b_0[V_w(I) - V_w(I-2)] - \{b_1 V_w(I-1) = b_2 V_w(I-2) + b_3 V_w(I-3) + b_4 V_w(I-4)\}$$

$$Z(0) = Z(-1) = z(-2) = Z(-3) = 0 \quad (27)$$

with $$b_0 = \left|\frac{1 + b_1 e^{-j\beta} + b_2 e^{-j2\beta} + b_3 e^{-j3\beta} + b_4 e^{-j4\beta}}{1 - e^{-j2\beta}}\right|$$
$$b_1 = -2e^{-\alpha}[\cos(\beta + \alpha) + \cos(\beta - \alpha)]$$
$$b_2 = 2e^{-2\alpha} + 4e^{-2\alpha}[\cos(\beta + \alpha)][\cos(\beta - \alpha)]$$
$$b_3 = -2e^{-3\alpha}[\cos(\beta + \alpha) + \cos(\beta + \alpha)]$$
$$b_4 = e^{-4\alpha}$$
$$\alpha = \frac{7\pi}{\sqrt{2}\ 32}$$

and $$\beta = 31\pi/32$$

These expressions are programmed into a computer such as computer 58 (shown in FIG. 3).

Finally in carrying out this invention it is desired to set forth the methods of analyses used to study the data collected, particularly the statistical techniques used to investigate the discriminating capability of the various features. The statistical techniques include the Baysian decision theory for multivariate Graussian process, and the concept of "divergence" as a measure of the performance of a specific feature or group of features. These techniques are described in full in such references as INFORMATION THEORY AND STATISTICS, by Kullback, S., John Wiley and Sons, London 1959, and the article by Marill, T., Green, D. M., "On the Effectiveness of Receptors in Recognition Systems," IEEE Transactors as Information Theory, pp. 11–17, January 1963. For example, there was employed a quadratic discriminant function that results from a Baysian decision rule to form the basis of a decision rule. Thus if P1 and M1 are the covariance matrix and mean vector for the class of normal cells whereas P2 and M2 are the corresponding variables for the class of abnormal cells, then we may establish a decision function defined by $$Q(X) = (X-M1)^T P1^{-1}(X-M1) - (X-M2)^T P2^{-1}(X-M2) = C$$

which would allow one to compute a number C for each cell depending upon the feature vector X measured for that cell. If the value of C for a cell is above some pre-defined value (decision level) then one would say that the cell is abnormal, and if it is below the level it would cause one to call the cell normal. In the problem of cell and smear discrimination, the value of the decision level can be adjusted to parametrically determine the statistical occurrance of errors of misclassification, i.e., the relative values of the false positive (normal cells misclassified as abnormal) and false negative (abnormal cells misclassified as normal). Other statistical decision procedures both linear and nonlinear may also be utilized such as the Fischer Discriminant described in the previous reference.

A computer program was written to carry out the Baysian discrimination, as well as compute the divergence number (a measure of power of features to discriminate cells) for the features being used. The specific components to be used for the pattern vector are requested and the statistics are calculated in the same manner as in the divergence analysis program. The means, standard deviation, scaling and correlation coefficients can be printed. The values of the Baysian quadratic discriminating function, as well as the Fischer Discriminant were then calculated and printed along with the maximum and minimum value for each class. A listing of the program and a typical printout per the method of this invention for the cells of FIGS. 7 and 8 was, as follows:

| Divergence = 66.0428 | | | |
|---|---|---|---|
| Difference of weighted distances from mean vectors | | | |
| Cell No. | Quad. Dist. | | F. Dist. |
| 177 | −22.8333 ↑ | | −5.1745 |
| 148 | − 7.2503 ↑ | Normal | −3.2750 |
| 187 | − 4.8001 ↑ | | −1.0751 |
| 173 | 59.6674 ↓ | | 3.2854 |
| 174 | 30.2046 ↓ | Malig. | 2.2887 |
| 175 | 27.5866 ↓ | | 0.0744 |
| Divergence with Lin. Disc. | | | 15.5274 |

OPERATION

Therefore, with the aforedescribed apparatus and theory this invention enabled the selection of various cell diffraction pattern features such as slope, energy and angular variance individually or collectively.

More particularly, a source of collimated light energy, as from a laser 16 or other source of coherent light is used to illuminate a cell image in a film holder or a real time transducer to generate an intensity profile of the cell structure. Actually, the image of the cell spatially modulates the collimated laser beam causing diffraction of the coherent light.

The next step of the process of this invention utilizes the Fourier transform lens 18 to collect the diffracted coherent light at a location behind the lens to create a diffraction pattern whose transverse spatial distribution of optical energy is functionally related to the modulated light immediately behind the image as expressed by equation (3). The location of the lens was established to be a distance of one focal length behind the image which then resulted in the establishment of the Fourier transform or diffraction pattern at a distance of one focal length behind the lens 18.

Since the diffraction pattern in the back focal plane, i.e. transform plane, may be too small for convenient observation, a short focal length magnifier 20 is then used to enlarge the diffraction pattern and project it in an enlarged area.

From this point the process can continue by one or the other of several known ways to classify the cell structure's diffraction pattern based upon its optical energy. In one such process the apparatus of FIG. 1 is employed to collect the diffraction pattern on the face of a solid-state electro-optical detector 22. With this apparatus the process of classification involves the creation of electrical energy to output terminals such as the two terminals 24 shown. A comparison of the electrical energy from each of the rings and from each of the wedges will provide not only signals of the optical energy but of the radial and angular location of same as will be further explained in reference to the process to be employed with the apparatus of FIGS. 1B and 4.

However, before entertaining an explanation of that apparatus it is also possible with the apparatus of FIG. 4 to obtain a photograph of the optical energy of the diffraction pattern for cell classification. More particularly, the diffraction pattern its collected upon a detector 116 that may simply be a camera back screen. In the case of screening exfoliated cervical cells to determine if they are cancer cells with which the apparatus and processes of this invention has been usefully employed it is possible to see distinctions in such spectral photographs between normal and cancer cells. Specifically, the spectral photograph of a normal cell will have angular symmetry of a "bulls-eye" pattern. characteristics of a transform of a circular opaque object. This readily contrasts with the broken or mottled pattern of the transform of an invasive cancel cell. In that the rules of the Patent Office do not permit the use of photographs in drawings of a patent, reference is made to the article in "The Journal of Histochemistry and Cytochemistry" aforementioned for a picture of what is possible by this apparatus. To classify the cell structure by this method only requires the viewing of the spectral photograph. It is also within the state of the art to use a real-time (optical) transducer, such as shown by FIG. 2A, to view the Fourier transform of the cell immediately, as it is projected from magnifier 112. It is also possible under the state of the art to generate the Fourier Transform pattern directly from the cell itself.

Finally with references to the operation of the apparatus of FIGS. 1A and 1B in obtaining a process of cell classification according to this invention the only apparatus and processes therefrom which differ from that aforedescribed is in reference to the use of masks 36 and 130 in combination with a photomultiplier 42. With this apparatus diffraction pattern 34 is projected by the enlarging microscope 20 on the face of mask 36 or 130. Mask 36 transmits by way of aperature 38 the spatial frequency spectrum of this diffraction pattern 34 to the ground glass screen of the photomultiplier 42. The mask 36 being mounted on frame 136 that is translatable along the X (optical) axis will transmit the radial variations of the spatial frequency spectrum which is one that expands in a cone fashion as the energy lines 30-32 indicate. As the photomultiplier 42 is moved in unison with the frame 136 for mask 36 along the optic axis, a point in the annulus in effect scans the diffraction pattern radially. During this multiposition scanning the potentiometer 144 provides a measurement of the spatial frequency scale which with the signals of light intensity of photomultiplier 42 will permit a graphical illustration of these scans as shown for the various cells of FIGS. 6 and 7 in according to equation (8).

Thereafter the mask 130 is substituted for mask 36 and driven by a motor 134 to revolve, as in a preferred form of apparatus, to provide angular scan data using a scanning hole at a predetermined frequency (as per example) 630 cycles per millimeter. This, as previously stated will provide a scan of optical energy passing through the hole as a function of the angular position in the Fourier transform; and an output signal of same from the photomultiplier according to the expression of equation (8). This would permit graphical illustration of the optical energy as per FIGS. 8 and 9 or 10, above described, to be related to a normal cell and an invasive cancer cell.

As may be appreciated by those skilled in the art the graphical illustrations may be provided by automatically plotting the radial/angular frequency content versus the spatial frequency/harmonic content by a plotter (not shown) in conjunction with the computer 204 providing discriminating readouts as aforesaid. It should also be appreciated that the apparatus for the process described herein may take still other forms without departing from the scope of this invention as set forth by the appended claims:

We claim:

1. Apparatus to investigate various morphological features of normal and cancerous cells comprising:
    a source of coherent light;
    a means to expand the light to cover a defined area;
    a first means in the path of the expanded light to present the morphological features of cells thereto such that the coherent light is scattered by these features in the path of said light;
    a first lens behind said first means to collect the scattered coherent light and project a diffraction pattern of said scattered coherent light to the focal point of said lens;
    a second lens behind said first lens to collect the diffraction pattern at the focal point of said first lens, enlarge said diffraction pattern and project said diffraction pattern; and an annular fiber optic disc of a plurality of fibers behind said second lens to collect said diffraction pattern with each of said fibers transmitting a portion of the energy of said diffraction pattern such that selecting outputs of certain fibers permit measuring the light intensity of such portion of the diffraction pattern corresponding to a predetermined radial distance and angular position from the center of the diffraction pattern.

2. Apparatus to investigate various structural or morphological features of normal and cancerous cells comprising:
   a source of coherent light;
   a means to enlarge the light;
   a first means to present an image of a cell in the path of said light;
   a lens behind said image to project a diffraction pattern of said image;
   a second means behind said lens to enlarge said diffraction pattern and project same; and
   a third means behind said second means to analyze said diffraction pattern quantitatively by providing signals of the light intensity representative of radial variation and angular variation of spatial frequency of optical energy off the center of the transform pattern, said third means including a first mask means for spatial distribution of optical energy of the diffraction pattern, said first mask means being adapted to translate along an axis of said aparatus and having an aperture for the transmission of the optical energy therethrough to thereby provide a scan of the radial variation of the spatial frequency of said optical energy; and a second mask means for said spatial distribution of optical energy, said second mask being adapted to be interchanged with said first mask to translate along an axis of said apparatus and having an aperture for the transmission of the optical energy therethrough which is emanating from said magnifier in a conical pattern to thereby provide a scan of the angular variation of the spatial frequency of said optical energy.

3. Apparatus to investigate various structural or morphological features of cells to determine whether same have malignant characteristics, said apparatus comprising:
   a source of collimated light;
   a cell image means located to be exposed to said light such that said image will cause diffraction of the coherent light of said source of collimated light;
   a convex lens located a predetermined distance behind said cell image means to collect the diffracted coherent light and transform same into a spatial distribution of optical energy in accordance with the expression, $$F(w_x, w_y) = \iint_{-\infty}^{\infty} f(x_o, y_o) e^{-j(w_x x_o + w_y y_o)} dx_o dy_o$$

where
   $F(w_x, w_y)$ is the distribution of the Fourier transform in rectangular coordinates
   f is the focal length
   $w_x$ is the transform x size scale
   $w_y$ is the transform y size scale
   xo is a position coordinate in the input plane
   yo is a position coordinate in the input plane perpendicular to the xo coordinate axis;
   a means one focal length from said lens to magnify said optical energy that will provide a measurable pattern of its radial and angular variation; and
   a means to select a measure of the pattern including a mask means for said spatial distribution of optical energy, said mask means being adapted to translate along an axis of said apparatus and having an aperture for the transmission of the optical energy therethrough to thereby provide a scan of the radial variation of the spatial frequency of said optical energy.

4. Apparatus to investigate various structural or morphological features of cells to determine whether same have malignant characteristics, said apparatus comprising:
   a source of collimated light,
   a cell image means located to be exposed to said light such that said image will cause diffraction of the coherent light of said source of collimated light;
   a convex lens located a predetermined distance behind said cell image means to collect the diffracted coherent light and transform same into a spatial distribution of optical energy in accordance with the expression, $$F(w_x, w_y) = \iint_{-\infty}^{\infty} f(x_o, y_o) e^{-j(w_x x_o + w_y y_o)} dx_o dy_o$$

where
   $F(w_x, w_y)$ is the distribution of the Fourier transform in rectangular coordinates
   f is the focal length
   $w_x$ is the transform x size scale
   $w_y$ is the transform y size scale
   xo is a position coordinate in the input plane
   yo is a position coordinate in the input plane perpendicular to the xo coordinate axis;
   a magnifier lens for said spatial distribution of optical energy located one focal length behind said convex lens that will provide pattern of optical energy having radial and angular variation; and
   a means to provide signals from said pattern including a first mask means for said spatial distribution of optical energy, said first mask means being adapted to translate along an axis of said apparatus and having an aperture for the transmission of the optical energy therethrough which is emanating from said magnifier to thereby provide signals indicating the radial variation of the spatial frequency of said optical energy and another mask mounting means between said means to magnify and said photomultiplier on the axis therebetween coincident with the axis of said source of collimated light, said another mask being also adaptable to translate along said axis and having an aperture to provide signals indicating angular variation of the spatial frequency of said optical energy as said mask mounting means is moved from one position to another position.

5. Apparatus to investigate various structural or morphological features of cells to determine whether same have malignant characteristics, said apparatus:
   a source of collimated light;
   an optical transducer cell image means located to be exposed to said light such that said image means located to be exposed to said light such that said image will cause diffraction of the coherent light of said source of collimated light;

a convex lens located a predetermined distance behind said cell image means to collect the diffracted coherent light and transform same into a spatial distribution of optical energy in accordance with the expression, $$F(w_x, w_y) = \iint_{-\infty}^{\infty} f(x_o, y_o) e^{-j(w_x x_o + w_y y_o)} dx_o dy_o$$

where
F($w_x$,$w_y$) is the distribution of the Fourier transform in rectangular coordinates
f is the focal length
$w_x$ is the transform x size scale
$w_y$ is the transform y size scale
xo is a position coordinate in the input plane
yo is a position coordinate in the input plane perpendicular to the xo coordinate axis;
a means to magnify said optical energy that will provide a mesurable pattern of its radial and angular variation; and
a fiber optic detector comprising a disc of fiber optic elements to receive said magnified optical energy, said detector having a disc of closely adjacent fiber optic elements that will transmit signals of the total light energy on the disc, said fiber optic elements providing signals of optical energy at a radial distance and angular position from the center of the transform plane.

6. Apparatus to investigate morphological features of normal and cancerous cells comprising:
a source of coherent light;
a means to enlarge the area of the source of coherent light;
a first means to present the morphological features of the cells in the direct path of said coherent light;
a convex lens behind said first means to project a diffraction pattern of the morphological features of the cells as impressed on said path of coherent light by said first means;
a second means behind said convex lens collecting the entire diffraction pattern on the path of said coherent light from the focal point of said convex lens, said second means also enlarging and projecting said entire diffraction pattern of the morphological features of the cells; and
a third means behind said second means, said third means having a face exposed to the entire, enlarged diffraction pattern, said face having means to produce signals from portions of the entire diffraction pattern to permit analyzation of said portions of said diffraction pattern by measuring the light intensity of said portions as a function of the radial distance from the center of the entire diffraction pattern.

7. The apparatus of claim 6 and further characterized by the third means also including means to provide signals from other portions of the entire diffraction pattern for the measuring of angular locations of the other portions.

8. The apparatus of claim 6 wherein the third means includes a solid state electronic sensor that will produce signals of radial and angular intensity of portions of the coherent light in the diffraction pattern appearing on semi-circular radial elements and finite length wedge elements forming said sensor.

9. The apparatus of claim 6 wherein the third means has fiber-optic elements arranged to be the face exposed to the entire, enlarged diffraction pattern that will permit the measurements to be made from signals from selected portions of fiber-optic elements.

10. The apparatus of claim 6 wherein the third means includes a first mask means for spatial distribution of optical energy of the diffraction pattern, said first mask means being adapted to translate along an axis of said apparatus and having an aperture for the transmission of the optical energy therethrough to thereby provide a scan of the radial variation of the spatial frequency of said optical energy; and a second mask means for said spatial distribution of optical energy, said second mask being adapted to be interchanged with said first mask to translate along an axis of said apparatus and having an aperture for the transmission of the optical energy therethrough which is emanating from said magnifier in a conical pattern to thereby provide a scan of the angular variation of the spatial frequency of said optical energy.

11. The apparatus of claim 6 wherein said second means includes a magnifier lens to provide a spatial distribution of optical energy in said entire diffraction pattern, said magnifier lens being located one focal length behind said convex lens.

* * * * *

UNITED STATES PATENT AND TRADEMARK OFFICE
CERTIFICATE OF CORRECTION

PATENT NO. : 4,150,360
DATED : April 17, 1979
INVENTOR(S) : Richard E. Kopp, et al.

It is certified that error appears in the above-identified patent and that said Letters Patent are hereby corrected as shown below:

[54] Title should read --- APPARATUS FOR CLASSIFYING BIOLOGICAL CELLS ---.

Column 1; Line 2, delete "METHOD AND"

Column 4; Line 6, delete "to" and insert therefor --- of ---.

Column 4; Line 12, delete "contract" and insert --- contrast ---.

Column 12; change Equation 20 to read ---

$$\int_{\Theta_1(I)}^{\Theta_2(I)} d\Theta \int_{g=500}^{h=600} \rho |F(\rho,\Theta)|^2 d\rho \sim \left[ \int_{g=500}^{h=600} \rho |F(\rho,\Theta)|^2 d\rho \right] \Delta\Theta$$

Signed and Sealed this

Eleventh Day of September 1979

[SEAL]

Attest:

LUTRELLE F. PARKER

Attesting Officer    Acting Commissioner of Patents and Trademarks